(12) United States Patent
Bombarda et al.

(10) Patent No.: US 7,183,410 B2
(45) Date of Patent: Feb. 27, 2007

(54) STABLE POLYMORPH OF FLIBANSERIN

(75) Inventors: Carlo Bombarda, Chester, VA (US); Enrica Dubini, Milan (IT); Antoine Ezhaya, Milan (IT); Heinrich Schneider, deceased, late of Ingelheim, DE (US); by Margarete Schneider, legal representative, Ingelheim (DE)

(73) Assignee: Bidachem S.p.A., Fornovo San Giovanna (IT)

(*) Notice: Subject to any disclaimer, the term of this patent is extended or adjusted under 35 U.S.C. 154(b) by 90 days.

(21) Appl. No.: 10/210,474

(22) Filed: Aug. 1, 2002

(65) Prior Publication Data

US 2003/0119850 A1   Jun. 26, 2003

Related U.S. Application Data

(60) Provisional application No. 60/329,435, filed on Oct. 15, 2001.

(30) Foreign Application Priority Data

Aug. 2, 2001   (EP)   ................... 01118593
Dec. 19, 2001   (EP)   ................... 01130180

(51) Int. Cl.
C07D 403/00   (2006.01)
(52) U.S. Cl. ............. 544/370; 544/366; 544/295; 514/254.06; 514/253
(58) Field of Classification Search ............ 544/370, 544/295, 366; 514/253, 252.13, 254.06
See application file for complete search history.

(56) References Cited

U.S. PATENT DOCUMENTS

| | | | |
|---|---|---|---|
| 3,406,178 A | 10/1968 | Crocker et al. | |
| 3,472,854 A | 10/1969 | Archer | |
| 4,200,641 A | 4/1980 | Vandenberk et al. | |
| 4,737,500 A | 4/1988 | Sorg | |
| 4,797,399 A | 1/1989 | Ueda et al. | |
| 4,859,692 A | 8/1989 | Bernstein et al. | |
| 4,886,803 A | 12/1989 | Sueda et al. | |
| 4,940,793 A | 7/1990 | Botre et al. | |
| 4,954,503 A | 9/1990 | Strupczewski et al. | |
| 5,036,088 A | 7/1991 | Kitaura et al. | |
| 5,576,318 A | 11/1996 | Bietti et al. | |
| 5,883,094 A * | 3/1999 | Fliri et al. .................. | 514/242 |
| 6,281,218 B1 * | 8/2001 | Cereda et al. ......... | 514/254.06 |
| 6,284,757 B1 | 9/2001 | Sanner | |
| 6,521,623 B1 | 2/2003 | Cereda et al. | |
| 6,586,435 B2 | 7/2003 | Cereda et al. | |
| 2003/0027823 A1 * | 2/2003 | Cereda et al. ........... | 514/234.5 |
| 2003/0060475 A1 | 3/2003 | Borsini et al. | |
| 2003/0083228 A1 | 5/2003 | Carpino et al. | |
| 2003/0104980 A1 | 6/2003 | Borsini et al. | |
| 2003/0119850 A1 | 6/2003 | Bombarda et al. | |
| 2004/0048877 A1 | 3/2004 | Friedl et al. | |
| 2004/0180904 A1 | 9/2004 | Beck | |

(Continued)

FOREIGN PATENT DOCUMENTS

EP   0200322   11/1986

(Continued)

OTHER PUBLICATIONS

Boehringer Ingelheim (IT), Prop INN, 1,3-Dihydro-1-[2-[4-[3[(trifluoromethyl)phenyl]-1-piperazinyl]-22h-benzimidazol-2-one, Drugs of the Future, 1998, 23(1):9-16.*

(Continued)

Primary Examiner—Thurman K. Page
Assistant Examiner—Chukwuma Nwaonicha
(74) Attorney, Agent, or Firm—Michael P. Morris; Mary-Ellen M. Devlin

(57) ABSTRACT

The invention relates to the polymorph A of flibanserin, to a technical process for the preparation thereof, as well as to the use thereof for preparing medicaments.

6 Claims, 1 Drawing Sheet

U.S. PATENT DOCUMENTS

| | | | |
|---|---|---|---|
| 2004/0235861 | A1 | 11/2004 | Borsini et al. |
| 2005/0065158 | A1 | 3/2005 | Naylor et al. |
| 2005/0159430 | A1 | 7/2005 | Bombarda et al. |
| 2005/0239798 | A1 | 10/2005 | Pyke |
| 2005/0245539 | A1 | 11/2005 | Mendla et al. |
| 2006/0014757 | A1 | 1/2006 | Pyke |
| 2006/0025420 | A1 | 2/2006 | Brauns et al. |

FOREIGN PATENT DOCUMENTS

| | | | |
|---|---|---|---|
| EP | 0 526 434 | A1 * | 2/1993 |
| EP | 0 526 434 | B1 | 2/1993 |
| EP | 0705832 | | 4/1996 |
| EP | 0816356 | | 1/1998 |
| EP | 0982030 | A2 | 3/2000 |
| EP | 1256343 | A1 | 11/2002 |
| GB | 2023594 | | 1/1980 |
| WO | WO 95/034555 | | 12/1995 |
| WO | WO 98/42344 | A1 | 10/1998 |
| WO | WO 00/028993 | | 5/2000 |
| WO | WO 01/021593 | | 3/2001 |
| WO | WO 03/013539 | | 2/2003 |
| WO | WO 03/035072 | | 5/2003 |

OTHER PUBLICATIONS

Cynthia Darlinton, Flibanserin, Current Opinion in CPNS Investigational Drugs, 1999 1(4):510-513.*
Borsini, F. et al; "BIMT 17, a 5-HT2A receptor antagonist and 5-HT1A receptor full agonist in rat cerebral cortex"; Naunyn-Schmiedeberg's Archives of Pharm., 352(3), 1995 pp. 276-282.
Giron, D; "Thermal analysis and calorimetric methods in the characterisation of polymorphs and solvates"; Thermochimica ACTA, Elsevier Science; 248; 1995; pp. 1-59.
Bernstein, J. et al; "Concomitant Polymorphs"; Angewandte Chemie, Int. Ed., 1999, pp. 3441-3461.
Borsini, F., "Method of Using Flibanserin for Neuroprotection"; U.S. Appl. No. 10/214,781, filed Aug. 8, 2002.
Darlington, C.; "Flibanserin", Current Opinion In CPNS Investigational Drugs; Bd 1 Nr. 4, 1999, pp. 510-513.
Borsini et al; Behavioral Effects of Flibanserin (BIMT 17), Sep. 1999, Pharmacology, Biochemistry and Behavior, vol. 64, Issue 1, see abstract.
Cools, A. R. "Depression and Psychosis" Behavioural Pharmacology of 5-HT, pp. 153-155 (1989).
Geyer, M. "5-HT2 antagonists increase tactile startle habituation in an animal model of habituation deficit in schizophrenia" Behavioural Pharmacology of 5-HT, pp. 243-246 (1989).
Bevan et al. "5-HT and Sexual Behaviour" Behavioural Pharmacology of 5-HT, pp. 33-34, 87-88 (1989).
Archer, T. "5HT, Pain and Anxiety" Behavioural Pharmacology of 5-HT, pp. 299-300 (1989).
Cloninger, C.R. "A Systematic Method for Clinical Description and Classification of Personality Variants" Arch. Gen. Psychiatry, vol. 44, pp. 573-588 (Jun. 1987).
Leonard, B. E. "Sub-types of serotonin receptors: biochemical changes and pharmacological consequences" International Clinical Psychopharmacology 7, 13-21 (1992).
Reikkinen et al. "The Effects of Increased Serotonergic and Decreased Cholinergic Activities on Spatial Navigation Performance in Rats" Pharmacology Biochemistry & Behavior, vol. 39, pp. 25-29 (1991).
Crook, T. and Lakin, M. "Effects of Ondansetron in Age-associated Memory Impairment" The role of ondansetron, a novel 5-HT3 antagonist, in the treatment of psychiatric disorders, 5th World Congress of Biochemical Psychiatry, pp. 21-23 (1991).
Jean L. Fourcroy "Female Sexual Dysfunction: Potential for Pharmacotherapy" Drugs 2003, vol. 63, No. 14, pp. 1445-1457.
Reuter, L. E. et al. "Electrophysiological examination of the effects of sustained flibanserin administration on serotonin receptors in rat brain" British J. of Pharm., 1999, vol. 126, No. 3, pp. 627-638.
Podhorna et al. "Flibanserin has anxiolytic effects without locomotor side effects in the infant rat ultrasonic vocalization model of anxiety" British J. of Pharm. 2000, vol. 130, No. 4, pp. 739-746.
Steiner, M. "Recognition of Premenstrual Dysphoric Disorder and Its Treatment" The Lancet, vol. 356, No. 9236, Sep. 30, 2000, pp. 1126-1127.
Dimmock, P. et al. "Efficacy of Selective Serotonin-Reuptake Inhibitors in Premenstrual Syndrome: A Systematic Review" The Lancet, vol. 356, No. 9236, Sep. 30, 2000, pp. 1131-1136.
Greene, T. "Protective Groups in Organic Synthesis", Havard University, pp. 10-17, 1981 (Wiley-Interscience Publication).
Chemical Abstract: Database Accession No. 98:16650-XP 002197885 Collino, F. et al.: Mannich bases of benzimidazoles, benzotriazoles and other analogous compounds, with pharmacological activity.
Chalmers et al., "Corticotrophin-releasing factor receptors: from molecular biology to drug design", TiPS vol. 17, pp. 166-172, Apr. 1996.
Lyrer, "Neue Ansatze in der Akutbehandlung des zerebrovaskularen Insultes" Schweiz. Med. Wochenschr., vol. 124, #45, 2005-2012 1994.
Frampton et al., Pentoxifylline (Oxpentiflline) A Review of its Therapeutic Efficacy in the Management of Peripheral Vascular and Cerebrovascular Disorders; (Drug Evaluation) Drugs and Aging 7(6), pp. 480-503, 1995.
Damour et al. CA 118-124537e (1992).
Awouters et al. CA 88-98788 (1977).
Vaudenberk et al. CA 88-50920n (1977).
Basson et al., "Report of the international consensus development conference on female sexual dysfunction: Definitions and Classifications", The Journal of Urology; vol. 163; pp. 888-893: Mar. 2000.
Invernizzi et al., "Flibanserin, a potential antidepressant drug, lowers 5-HT and raises dopamine and noradrenaline in the rat prefrontal cortex dialysate: role of 5-HT$_{1A}$ receptors" British Journal of Pharmacology, vol. 139, pp. 1281-1288, Jun. 2003.

* cited by examiner

STABLE POLYMORPH OF FLIBANSERIN

RELATED APPLICATIONS

Benefit of U.S. Provisional Application Ser. No. 60/329,435, filed on Oct. 15, 2001 is hereby claimed, and said application is herein incorporated by reference in its entirety.

FIELD OF THE INVENTION

The invention relates to the polymorph A of flibanserin, to a technical process for the preparation thereof, as well as to the use thereof for preparing medicaments.

BACKGROUND OF THE INVENTION

The compound 1-[2-(4-(3-trifluoromethyl-phenyl)piperazin-1-yl)ethyl ]-2,3-dihydro-1H-benzimidazol -2-one (flibanserin) is disclosed in form of its hydrochloride in European Patent Application EP-A-526434 and has the following chemical structure:

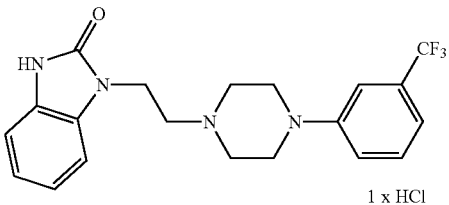

1 x HCl

Flibanserin shows affinity for the $5\text{-HT}_{1A}$ and $5\text{-HT}_2$-receptor. It is therefore a promising therapeutic agent for the treatment of a variety of diseases, for instance depression, schizophrenia, Parkinson, anxiety, sleep disturbances, sexual and mental disorders and age associated memory impairment.

A certain phamaceutical activity is of course the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is absolutely essential to prevent the use of pharmaceutical compositions which contain, in addition to the actual active substance, breakdown products thereof, for example. In such cases the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g. by grinding. Since breakdown of the pharmaceutically active substance as a side effect of the grinding (or micronising) has to be avoided as far as possible, in spite of the hard conditions required during the process, it is absolutely essential that the active substance should be highly stable throughout the grinding process. Only if the active substance is sufficiently stable during the grinding process is it possible to produce a homogeneous pharmaceutical formulation which always contains the specified amount of active substance in reproducible manner.

Another problem which may arise in the grinding process for preparing the desired pharmaceutical formulation is the input of energy caused by this process and the stress on the surface of the crystals. This may in certain circumstances lead to polymorphous changes, to a change in the amorphous configuration or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

Apart from the requirements indicated above, it should be generally borne in mind that any change to the solid state of a pharmaceutical composition which is capable of improving its physical and chemical stability gives a significant advantage over less stable forms of the same medicament.

The aim of the invention is thus to provide a new, stable crystalline form of the compound flibanserin which meets the stringent requirements imposed on pharmaceutically active substances as mentioned above.

DETAILED DESCRIPTION OF THE INVENTION

Figure 1:
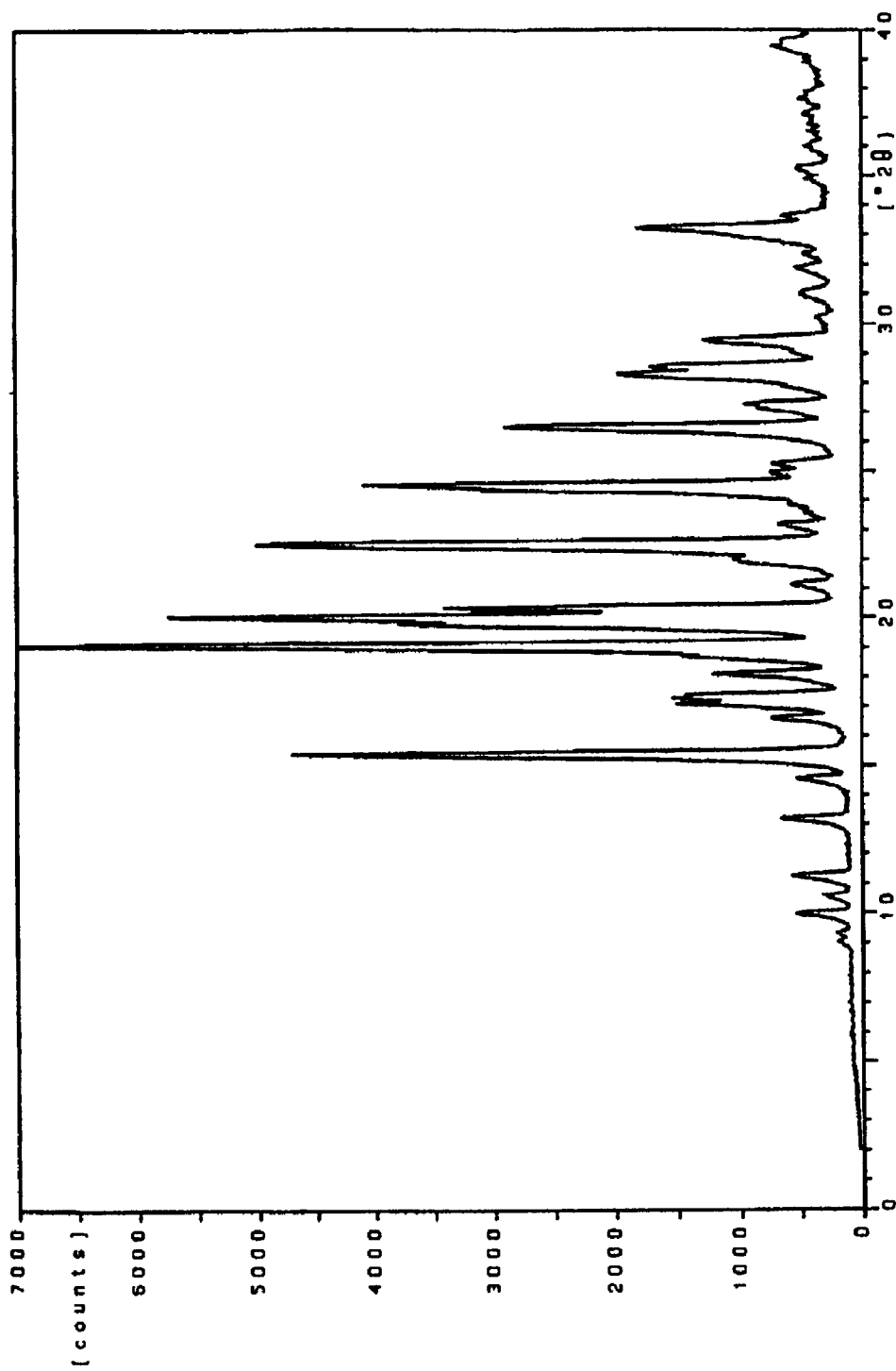
FIG. 1 shows the X-ray powder diffraction pattern of polymorph A of flibanserin.

Surprisingly, it has been found that the free base of flibanserin in a specific polymorphic form fulfills the requirements mentioned hereinbefore.

Moreover it has been found that, depending on the choice of conditions which can be applied during the synthesis of flibanserin the free base occurs in different crystalline modifications, polymorphs A and B.

It has been found that these different modifications can be deliberately produced by a suitable choice of the process conditions used in the manufacturing process.

Surprisingly, it has been found that polymorph A, which can be obtained in crystalline form by choosing specific reaction conditions, meets the stringent requirements mentioned above and thus solves the problem on which the present invention is based. Accordingly the present invention relates to polymorph A of flibanserin.

Polymorph A of flibanserin is characterised by a melting point of about 161° C. (determined via DSC; heating rate 10 K/min). 161° C. as determined using DSC.

Polymorph B, the less stable modification of flibanserin displays a melting point of about 120° C. (determined via DSC; heating rate 10 K/min). Whereas polymorph B shows little stability under the effects of for instance mechanical stress produced by grinding, polymorph A turned out to fulfill the aforementioned stability requirements.

According to another aspect, the present invention relates to a process for the manufacture of polymorph A of flibanserin in technical scale. The process according to the invention is illustrated in diagram 1.

Diagram 1:

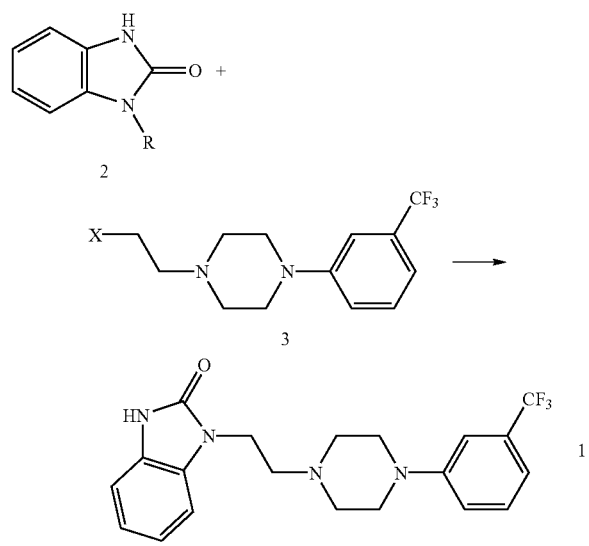

The benzimidazolone 2 is reacted with the piperazine-derivative 3 under basic reaction conditions in a suitable solvent to lead to 1. In 2 the group R denotes an amino protecting group. The protecting group used may be any of the groups commonly used to protect the amino function. Examples include groups selected from alkyl, substituted alkyl, heterosubstituted alkyl, unsaturated alkyl, alkyl substituted heteroatoms, substituted or unsubstituted phenyl, substituted or unsubstituted benzyl, alkyloxycarbonyl groups and aryloxycarbonyl groups. Preferred protecting groups are selected from butyl, 1,1-diphenylmethyl, methoxymethyl, benzyloxymethyl, trichloroethoxymethyl, pyrrolidinomethyl, cyanomethyl, pivaloyloxymethyl, allyl, 2-propenyl, t-butyldimethylsilyl, methoxy, thiomethyl, 4-methoxyphenyl, benzyl, 4-methoxybenzyl, 2,4-dimethoxybenzyl, 2-nitrobenzyl, t-butoxycarbonyl, benzyloxycarbonyl, phenoxy carbonyl, 4-chloro-phenoxycarbonyl, 4-nitro-phenoxycarbonyl, methoxycarbonyl and ethoxycarbonyl. Among them the preferred protecting groups are selected from t-butoxycarbonyl, ethoxycarbonyl, methoxycarbonyl, benzyloxycarbonyl, phenoxycarbonyl and 2-propenyl, the latter being most preferred. X in 3 represents a leaving group selected from chlorine, bromine, iodine, methanesulphonate, trifluoromethanesulphonate or para-toluenesulphonate. Preferably X denotes chlorine, bromine or iodine, chlorine being most preferred. Suitable solvents are selected from water, alcohols and mixtures of water with alcohols, polar aprotic solvents and mixtures thereof with water. Preferred solvents are selected from the group consisting of dimethylformamid, dimethylsulfoxid, acetonitrile, tetrahydrofurane, dioxane, methanol, ethanol isopropanaol and mixtures of one or several of the aformentioned solvents with water. Preferred solvents are those being readily miscible with water. Preferably, a mixture of water with one of the alcohols methanol, ethanol or isopropanol is used as the solvent. In a preferred embodiment a mixture of water and isopropanol is used as the solvent. The base used may be an alkali metal- or alkaline earth metal carbonate of lithium, sodium, potassium, calcium such as sodium carbonate, lithium carbonate, potassium carbonate, calcium carbonate and preferably potassium carbonate. It is also possible to use the hydrogen carbonates of lithium, sodium and potassium. Preferably, the alkali metal- or alkaline earth metal hydroxides of lithium, sodium, potassium, magnesium, calcium, but preferably sodium hydroxide, potassium hydroxide, lithium hydroxide and calcium hydroxide in alcohols or water may also be used. Most preferred base is sodium hydroxide. The base is preferably added in form of its aqueous solution, preferably in form of concentrated aqueous solutions, for example in concentrations between 30–50% weight/volume. In a preferred embodiment aqueous sodium hydroxide solution in a concentration of about 45% weight/volume is used.

The compounds 2 and 3 are introduced into the reaction in a molar ratio of between 1:1 to 1:2, preferably in a molar ratio of between 1:1.1 to 1:1.5.

As mentioned hereinbefore a mixture of water and isopropanol is used as a preferred solvent mixture for the conduction of the process according to the invention. In this solvent mixture the weight-ratio of water to isopropanol in the preferred solvent mixture is between 10:1 and 1:1, more preferred between 8:1 and 3:1, particular preferred between 7:1 and 5:1. Per mol of compound 2 about 2–10 kg, preferably 3–8 kg, more preferred 4–7 kg of the aforementioned solvent mixture are used. In a preferred embodiment the reaction is conducted using aqueous sodium hydroxide solution in a concentration of about 45% weight/volume as the base. Per mol of 2 about 0.1–1.5 kg, preferably 0.2–1.0 kg, particularly preferred 0.3–0.6 kg of the aforementioned sodium hydroxide solution are used. The reaction mixture containing 2, 3 and the base in the aforementioned suitable solvent is preferably heated to at least 50° C. In a preferred embodiment the reaction temperature is in a range of between 60° C. to the boiling point of the solvent. Particularly preferred is a temperature between 70–90° C. The reaction mixture is heated at the aformentioned temperature for about 10 minutes to about 12 hours, preferably for about 15 minutes to about 6 hours, more preferably for about 30 minutes to about 3 hours. The reaction mixture is preferably heated at the aformentioned temperature for about 45 to 60 minutes.

Subsequently the protective group R is cleaved. The cleaving conditions depend on the choice of group R. If R denotes for instance benzyl, cleavage is conducted via hydrogenation in acetic acid in the presence of an appropriate catalyst (e.g. Pd on charcoal) or it can be cleaved in aqueous HBr. In case R is methoxycarbonyl, ethoxycarbonyl, phenoxy carbonyl, 4-nitrophenoxycarbonyl it can be cleaved for example by using aqueous alkaline solutions such as NaOH (aq) or KOH(aq). In case R is t-butoxycarbonyl it can be cleaved for instance in aqueous HCl or HBr. In case R denotes 2-propenyl, the particularly preferred protective group according to the invention, cleavage of R is effected via acidic reaction conditions. In a particularly preferred process according to the invention the 2-propenyl group is cleaved by using a strong mineral acid, preferably an acid selected from the group consisting of hydrobromic acid, hydrochloric acid and sulfuric acid, more preferably hydrochloric acid. Hydrochloric acid can be added in gaseous form or in form of its aqueous solutions, the addition of aqueous solutions being preferred. Particularly preferred is the addition of hydrochloric acid in form of its concentrated solution (about 36% weight/volume). Per mol 2 at least one mol of hydrochloric acid is to be added. Preferably the amount of added concentrated hydrochloric acid (36% weight/volume) per mol 2 is between 50–500 g, more preferred between 80–250 g. Particularly preferred about 120–160 g of concentrated (36% w/v) aqueous hydrochloric acid are added per mol 2 used. Additional water can be optionally added. At a temperature of about 70–90° C. about 30–70%, preferably about 35–60% of the solvent is removed via distillation. At a temperature of about 60–80° C. the pH of the remaining residue is adjusted to about 5–9, preferably to about 6–8 by addition of aqueous sodium hydroxide (45% w/v). At a temperature of about 40–55° C. the pH is adjusted to about 8–9 by addition of aqueous sodium hydroxide (45% w/v). Subsequently the mixture is cooled to about 20–40° C., preferably about 30–35° C. and centrifuged. The residue thus obtained is washed with about 100 to 750 ml water per mol introduced 2, preferably with about 200 to 500, particularily preffered with about 300 to 400 ml water per mol introduced 2 and isopropanol (about 50 to 250 g per mol 2, preferably about 100 to 200 g per mol 2) and then with water until chlorides elimination. Optionally the product thus obtained can be subjected to another purification step. Preferably, said purification is conducted via crystallization of 1 from fror instance acetone.

One aspect of the present invention relates to flibanserin polymorph A obtainable via the method described above.

The following example of synthesis serves to illustrate a method of preparing polymorph A of flibanserin. It is to be regarded only as a possible method described by way of example, without restricting the invention to its contents.

EXAMPLE 375 kg of 1-[(3-trifluoromethyl)phenyl]-4-(2-cloroethyl) piperazin are charged in a reactor with 2500 kg of water and 200 kg of aqueous Sodium Hydroxide 45%. Under stirring 169.2 kg of 1-(2-propenyl)-1,3-dihydro-benzimidazol-2H-one, 780 kg of isopropanol, 2000 kg of water and 220 kg of aqueous Sodium Hydroxide 45% are added. The reaction mixture is heated to 75–85° C. and 160 kg of concentrated hydrochloric acid and 200 kg of water are added. The reaction mixture is stirred at constant temperature for about 45 minutes. After distillation of a mixture of water and Isopropanol (about 3000 kg) the remaining residue is cooled to about 65–75° C. and the pH is adjusted to 6.5–7.5 by addition of 125 kg of aqueous Sodium Hydroxide 45%. After cooling to a temperature of 45–50° C., the pH value is adjusted to 8–9 by addition of about 4 kg of aqueous Sodium Hydroxide 45%. Subsequently the mixture is cooled to 30–35° C. and centrifuged. The residue thus obtained is washed with 340 l of water and 126 l of isopropanol and then with water until chlorides elimination. The wet product is dried under vacuum at a temperature of about 45–55° C. which leads to 358 kg of crude flibanserin polymorph A. The crude product thus obtained is loaded in a reactor with 1750 kg of Acetone and the resulting mixture is heated under stirring until reflux. The obtained solution is filtered and the filtrate is concentrated by distillation. The temperature is maintained for about 1 hour 0–5° C., then the precipitate solid is isolated by filtration and dried at 55° C. for at least 12 hours.

The final yield is 280 kg of pure flibanserin polymorph A.

As mentioned hereinbefore flibanserin polymorph A was characterised by DSC (Differantial Scanning Calorimetry). The peak temperature (endothermic maximum) determined for polymorph A is about 161° C. For the characterization via DSC a Mettler TA 3000 System equipped with TC 10-A processor and DSC 20 cell was applied. The heating rate was 10 K/min.

The flibanserin polymorph A was additionally characterised by powder x-ray diffractometry. The x-ray powder diffraction pattern for polymorph A was obtained according to the following conditions:

| Equipment: | Philips PW 1800/10 diffractometer equipped with a digital microvax 2000. |
|---|---|
| Setting parameters: | X-ray |
| Type tube: | Cu (long fine focus) |
| Wavelenghts (λ): | $K\alpha_1$ = 1.54060 Å |
| | $K\alpha_2$ = 1.54439 Å |
| Intensity ratio (α2/α1): | 0.500 |
| Start angle [°2Θ]: | 2.000 |
| End angle [°2Θ]: | 60.000 |
| Step size [°2Θ]: | 0.020 |
| Maximum intensity[s]: | 7310.250 |
| Type of scan: | continuous |
| Minimum peak tip width: | 0.00 |
| Maximum peak tip width: | 1.00 |
| Peak base width: | 2.00 |
| Minimum significance: | 0.75 |
| Number of peaks: | 69 |
| Generator: | high voltage: 50 KV |
| | tube current: 30 mA |

The x-ray powder diffraction pattern obtained for polymorph A is illustrated in FIG. 1. The appropriate values are shown below in Table 1.

TABLE 1

| Angle [°2Θ] | d-value α1 [Å] | d-value α2 [Å] | Peak width [°2Θ] | Peak int [counts] | Back. int [counts] | Rel. int [%] | Signif. |
|---|---|---|---|---|---|---|---|
| 5.195 | 16.9967 | 17.0390 | 0.960 | 8 | 69 | 0.1 | 1.05 |
| 9.045 | 9.7689 | 9.7931 | 0.100 | 92 | 96 | 1.3 | 0.97 |
| 9.335 | 9.4660 | 9.4896 | 0.080 | 114 | 98 | 1.6 | 0.88 |
| 10.025 | 8.8160 | 8.8379 | 0.140 | 400 | 100 | 5.5 | 7.18 |
| 10.595 | 8.3430 | 8.3637 | 0.140 | 204 | 102 | 2.8 | 3.46 |
| 11.290 | 7.8309 | 7.8503 | 0.140 | 467 | 104 | 6.4 | 6.91 |
| 13.225 | 6.6891 | 6.7058 | 0.180 | 548 | 112 | 7.5 | 13.10 |
| 14.595 | 6.0642 | 6.0793 | 0.180 | 404 | 121 | 5.5 | 9.17 |
| 15.460 | 5.7268 | 5.7410 | 0.140 | 4186 | 125 | 57.3 | 23.20 |
| 16.655 | 5.3185 | 5.3317 | 0.200 | 515 | 130 | 7.0 | 12.38 |
| 17.085 | 5.1856 | 5.1985 | 0.100 | 1347 | 132 | 18.4 | 2.78 |
| 17.285 | 5.1260 | 5.1388 | 0.060 | 1399 | 135 | 19.1 | 2.26 |
| 17.420 | 5.0866 | 5.0992 | 0.100 | 1204 | 135 | 16.5 | 4.71 |
| 18.140 | 4.8863 | 4.8984 | 0.180 | 1043 | 139 | 14.3 | 13.14 |
| 18.650 | 4.7538 | 4.7656 | 0.120 | 1063 | 142 | 14.5 | 0.91 |
| 19.140 | 4.6332 | 4.6447 | 0.140 | 7310 | 144 | 100.0 | 32.77 |
| 19.820 | 4.4757 | 4.4869 | 0.160 | 3624 | 146 | 49.6 | 9.02 |
| 20.080 | 4.4184 | 4.4294 | 0.140 | 5402 | 149 | 73.9 | 21.06 |
| 20.385 | 4.3530 | 4.3638 | 0.160 | 2652 | 149 | 36.3 | 23.25 |
| 21.215 | 4.1845 | 4.1949 | 0.160 | 369 | 154 | 5.0 | 5.78 |
| 21.890 | 4.0570 | 4.0670 | 0.200 | 773 | 156 | 10.6 | 3.09 |
| 22.630 | 3.9259 | 3.9357 | 0.280 | 4277 | 161 | 58.5 | 74.66 |
| 23.210 | 3.8291 | 3.8386 | 0.120 | 484 | 164 | 6.6 | 3.33 |
| 24.355 | 3.6516 | 3.6607 | 0.060 | 2725 | 169 | 37.3 | 1.16 |
| 24.610 | 3.6144 | 3.6234 | 0.140 | 3540 | 172 | 48.4 | 17.08 |
| 24.995 | 3.5596 | 3.5684 | 0.100 | 529 | 174 | 7.2 | 1.01 |
| 25.260 | 3.5228 | 3.5316 | 0.120 | 557 | 174 | 7.6 | 3.02 |
| 26.575 | 3.3514 | 3.3597 | 0.240 | 2421 | 182 | 33.1 | 42.58 |
| 27.155 | 3.2811 | 3.2893 | 0.140 | 676 | 185 | 9.2 | 1.32 |
| 27.310 | 3.2629 | 3.2710 | 0.100 | 767 | 185 | 10.5 | 2.75 |
| 27.865 | 3.1991 | 3.2071 | 0.120 | 420 | 188 | 5.7 | 1.08 |

TABLE 1-continued

| Angle [°2Θ] | d-value α1 [Å] | d-value α2 [Å] | Peak width [°2Θ] | Peak int [counts] | Back. int [counts] | Rel. int [%] | Signif. |
|---|---|---|---|---|---|---|---|
| 28.210 | 3.1608 | 3.1686 | 0.100 | 1467 | 190 | 20.1 | 0.79 |
| 28.325 | 3.1482 | 3.1560 | 0.140 | 1789 | 190 | 24.5 | 4.41 |
| 28.650 | 3.1132 | 3.1210 | 0.180 | 1204 | 190 | 16.5 | 11.65 |
| 29.520 | 3.0234 | 3.0309 | 0.220 | 1011 | 196 | 13.8 | 15.74 |
| 30.250 | 2.9521 | 2.9594 | 0.120 | 159 | 199 | 2.2 | 1.22 |
| 31.105 | 2.8729 | 2.8800 | 0.360 | 282 | 204 | 3.9 | 8.14 |
| 31.905 | 2.8026 | 2.8096 | 0.100 | 339 | 207 | 4.6 | 0.96 |
| 32.350 | 2.7651 | 2.7720 | 0.120 | 237 | 210 | 3.2 | 3.01 |
| 33.300 | 2.6884 | 2.6950 | 0.180 | 1347 | 216 | 18.4 | 14.06 |
| 33.640 | 2.6620 | 2.6686 | 0.100 | 404 | 216 | 5.5 | 1.45 |
| 34.880 | 2.5701 | 2.5765 | 0.200 | 202 | 222 | 2.8 | 1.04 |
| 35.275 | 2.5422 | 2.5486 | 0.240 | 299 | 225 | 4.1 | 4.84 |
| 36.055 | 2.4890 | 2.4952 | 0.280 | 202 | 228 | 2.8 | 3.78 |
| 36.910 | 2.4333 | 2.4393 | 0.320 | 169 | 234 | 2.3 | 0.90 |
| 37.160 | 2.4175 | 2.4235 | 0.120 | 216 | 234 | 3.0 | 2.14 |
| 37.680 | 2.3853 | 2.3912 | 0.240 | 240 | 237 | 3.3 | 1.58 |
| 39.435 | 2.2831 | 2.2888 | 0.280 | 449 | 246 | 6.1 | 2.67 |
| 39.675 | 2.2698 | 2.2755 | 0.080 | 396 | 246 | 5.4 | 0.82 |
| 40.325 | 2.2347 | 2.2403 | 0.160 | 520 | 250 | 7.1 | 0.95 |
| 40.930 | 2.2031 | 2.2086 | 0.120 | 480 | 253 | 6.6 | 2.66 |
| 41.445 | 2.1769 | 2.1823 | 0.240 | 372 | 256 | 5.1 | 2.65 |
| 41.990 | 2.1499 | 2.1552 | 0.120 | 538 | 259 | 7.4 | 1.31 |
| 42.670 | 2.1172 | 2.1225 | 0.160 | 428 | 262 | 5.9 | 1.45 |
| 43.145 | 2.0950 | 2.1002 | 0.120 | 433 | 266 | 5.9 | 1.50 |
| 44.190 | 2.0478 | 2.0529 | 0.160 | 376 | 269 | 5.1 | 0.89 |
| 46.095 | 1.9675 | 1.9724 | 0.160 | 279 | 279 | 3.8 | 0.86 |
| 46.510 | 1.9509 | 1.9558 | 0.240 | 310 | 282 | 4.2 | 0.87 |
| 48.305 | 1.8826 | 1.8872 | 0.200 | 506 | 292 | 6.9 | 2.06 |
| 48.900 | 1.8610 | 1.8657 | 0.240 | 615 | 296 | 8.4 | 1.67 |
| 50.330 | 1.8115 | 1.8160 | 0.160 | 437 | 303 | 6.0 | 1.73 |
| 51.035 | 1.7881 | 1.7925 | 0.080 | 416 | 306 | 5.7 | 0.93 |
| 53.550 | 1.7099 | 1.7141 | 0.480 | 177 | 317 | 2.4 | 2.84 |
| 54.500 | 1.6823 | 1.6865 | 0.400 | 130 | 324 | 1.8 | 1.37 |
| 55.420 | 1.6565 | 1.6606 | 0.320 | 130 | 328 | 1.8 | 1.72 |
| 56.220 | 1.6348 | 1.6389 | 0.320 | 121 | 331 | 1.7 | 0.87 |
| 56.770 | 1.6203 | 1.6243 | 0.240 | 142 | 335 | 1.9 | 1.59 |
| 57.405 | 1.6039 | 1.6079 | 0.240 | 112 | 339 | 1.5 | 1.19 |
| 58.500 | 1.5764 | 1.5804 | 0.240 | 67 | 342 | 0.9 | 1.57 |

In the light of the pharmaceutical efficacy of flibanserin, the present invention furthermore relates to the use of flibanserin polymorph A as a medicament.

A further aspect of the present invention relates to the use of flibanserin polymorph A for preparing a pharmaceutical composition for treating diseases in which the use of compounds displaying affinity for the 5-$HT_{1A}$ and 5-$HT_2$-receptor may have a therapeutic benefit.

A further aspect of the present invention relates to the use of flibanserin polymorph A for preparing a pharmaceutical composition for treating a disease seleceted from depression, schizophrenia, Parkinson, anxiety, sleep disturbances, sexual and mental disorders and age associated memory impairment.

In particular, the instant invention relates to the use of flibanserin polymorph A for the preparation of a medicament for the treatment of disorders of sexual desire.

In a preferred embodiment the invention relates to the use of flibanserin polymorph A for the preparation of a medicament for the treatment of disorders selected from the group consisting of Hypoactive Sexual Desire Disorder, loss of sexual desire, lack of sexual desire, decreased sexual desire, inhibited sexual desire, loss of libido, libido disturbance, and frigidity.

Particular preferred according to the invention is the use of flibanserin polymorph A for the preparation of a medicament for the treatment of disorders selected from the group consiting of Hypoactive Sexual Desire Disorder, loss of sexual desire, lack of sexual desire, decreased sexual desire, inhibited sexual desire.

In a particularily preferred embodiment the invention relates to the use of flibanserin polymorph A for the preparation of a medicament for the treatment of disorders selected from the group of Hypoactive Sexual Desire Disorder and loss of sexual desire.

The aforementioned therapeutic effects of flibanserin polymorph A can be achieved in men and women. However, according to a further aspect of the invention the use of flibanserin polymorph A for the preparation of a medicament for the treatment of female sexual dysfunction is preferred.

The beneficial effects of flibanserin polymorph A can be observed regardless of whether the disturbance existed lifelong or was acquired, and independent of etiologic origin (organic—both, physically and drug induced—, psychogen, a combination of organic—both, physically and drug induced—, and psychogen, or unknown).

As a further feature of the present invention there are provided pharmaceutical compositions comprising as an active ingredient flibanserin polymorph A in addition with one or more pharmaceutical carrier, diluents or excipients. For pharmaceutical administration flibanserin polymorph A may be incorporated into the conventional pharmaceutical preparation in solid, liquid or spray form. The composition may, for example, be presented in a form suitable for oral, rectal, parenteral administration or for nasal inhalation: preferred forms includes for example, capsules, tablets, coated tablets, ampoules, suppositories and nasal spray. The active ingredient may be incorporated in excipients or carriers conventionally used in pharmaceutical compositions such as, for example, talc, arabic gum, lactose, gelatine, magnesium stearate, corn starch, acqueous or non acqueous vehicles, polyvynil pyrrolidone, semisynthetic gliceridies of fatty acids, benzalconium chloride, sodium phosphate, EDTA, polysorbate 80. The compositions are advantageously formulated in dosage units, each dosage unit being adapted to supply a single dose of the active ingredient. Each dosage unit may conveniently contain from 0,01 mg to 100 mg, preferably from 0,1 to 50 mg.

We claim:

1. A process for preparing form A of flibanserin 1 having an endothermic maximum at about 161° C. which occurs during thermal analysis using DSC,

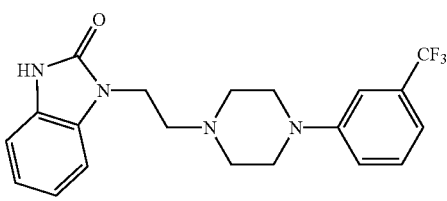

said process comprising:

(a) reacting a benzimidazolone 2

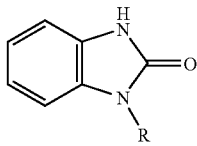

wherein R denotes a suitable amino protecting group, with a piperazine 3

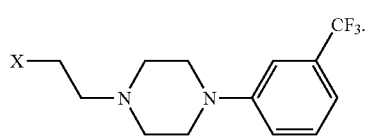

wherein X is a leaving group selected from chlorine, bromine, iodine, methanesulphonate, trifluoromethanesulphonate and para-toluenesulphonate, in a suitable solvent selected from water, alcohols, mixtures of water with alcohols, polar aprotic solvents and mixtures of polar aprotic solvents with water, in the presence of a suitable base, and (b) cleaving the amino protecting group R under suitable cleaving conditions.

2. A process according to claim 1, wherein the reaction of 2 with 3 is conducted at a temperature of at least 50° C.

3. A process according to claim 2, wherein heating is conducted for about 10 minutes to about 12 hours.

4. A process for preparing flibanserin 1 comprising form A having an endothermic maximum at about 161° C. which occurs during thermal analysis using DSC,

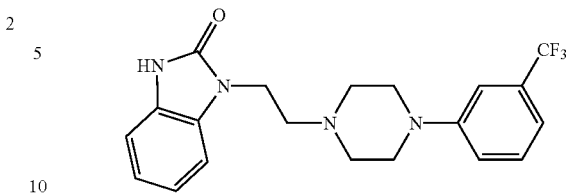

said process comprising:
(a) reacting a benzimidazolone 2

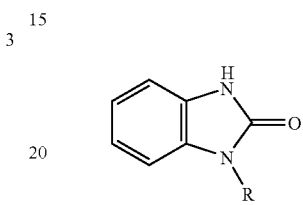

wherein R denotes a suitable amino protecting group, with a piperazine 3

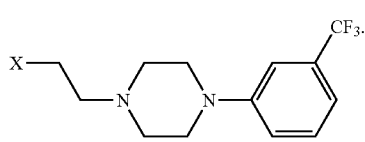

5. A process according to claim 4, wherein the reaction of 2 with 3 is conducted at a temperature of at least 50° C.

6. A process according to claim 5, wherein heating is conducted for about 10 minutes to about 12 hours.

* * * * *